US008193465B2

(12) United States Patent
Yang et al.

(10) Patent No.: US 8,193,465 B2
(45) Date of Patent: Jun. 5, 2012

(54) ELECTRONIC DEVICE AND METHOD OF USING THE SAME

(76) Inventors: Chang Ming Yang, Miaoli (TW); Tzu Lin Yang, Taipei (TW); Ching Wen Yang, Taipei (TW); Hao Yang, Taipei (TW)

( * ) Notice: Subject to any disclaimer, the term of this patent is extended or adjusted under 35 U.S.C. 154(b) by 92 days.

(21) Appl. No.: 12/053,553

(22) Filed: Mar. 22, 2008

(65) Prior Publication Data
US 2008/0230363 A1   Sep. 25, 2008

Related U.S. Application Data

(63) Continuation-in-part of application No. PCT/CN2005/001520, filed on Sep. 21, 2005.

(51) Int. Cl.
*H01H 3/02* (2006.01)

(52) U.S. Cl. ....................... 200/512; 200/85 R

(58) Field of Classification Search ................ 200/85 A, 200/85 R, 512
See application file for complete search history.

(56) References Cited

U.S. PATENT DOCUMENTS

| | | | | |
|---|---|---|---|---|
| 3,700,836 A | * | 10/1972 | Rackson | 200/52 R |
| 4,517,424 A | * | 5/1985 | Kroczynski | 200/52 R |
| 4,526,948 A | | 7/1985 | Resnick | |
| 4,635,646 A | | 1/1987 | Gilles et al. | |
| 4,660,033 A | * | 4/1987 | Brandt | 340/825.72 |
| 4,724,845 A | * | 2/1988 | Callahan | 600/531 |
| 4,872,008 A | * | 10/1989 | Ohtsuka et al. | 341/26 |
| 4,939,326 A | * | 7/1990 | Weinblatt | 200/506 |
| 5,019,950 A | * | 5/1991 | Johnson | 362/130 |
| 5,986,221 A | * | 11/1999 | Stanley | 177/136 |
| 6,107,585 A | * | 8/2000 | Gehr | 200/505 |
| 6,600,120 B1 | | 7/2003 | Marmaropoulos et al. | |
| 6,642,467 B2 | | 11/2003 | Farringdon | |
| 6,696,653 B1 | * | 2/2004 | Smith et al. | 200/85 R |
| 7,207,331 B2 | * | 4/2007 | Mashak | 128/204.21 |
| 2005/0156486 A1 | | 7/2005 | Orten | |

FOREIGN PATENT DOCUMENTS

| | | |
|---|---|---|
| CN | 1618395 | 5/2005 |
| CN | 1366308 | 7/2005 |
| DE | 29717348 | 2/1998 |
| JP | 57-045841 A | 3/1982 |
| JP | 60114234 A | 6/1985 |
| JP | 60-156631 A | 8/1985 |
| JP | 05-094919 A | 4/1993 |
| JP | 07-029728 A | 1/1995 |
| JP | 2001-333899 A | 12/2001 |
| JP | 2005-522292 T | 7/2005 |
| WO | 03-087737 A1 | 10/2003 |

OTHER PUBLICATIONS

International Search Report (PCT/CN2005/001520), completed Jun. 19, 2006.
English translation of an Official Action issued Jan. 4, 2011, by the Japan Patent Office in related Japanese Patent Application No. JP-2008-531504 (2 pages).

(Continued)

*Primary Examiner* — Elvin G Enad
*Assistant Examiner* — Lisa Klaus
(74) *Attorney, Agent, or Firm* — Osha • Liang LLP

(57) ABSTRACT

An electronic device which includes a resilient piece, base plate and electronic source. The upper conductor is located on the resilient piece; the base plate is connected to the resilient piece, with a space between the two. The lower conductor is located on the base plate, and there is a crevice between the lower conductor and the upper conductor. The electronic source electrically connected to the upper conductor and the lower conductor. The sensor device is located on the base plate. Utilizing this structure, the electronic device can, based on the user's needs, perform testing of the subject's physiological status or test a specific site that is pressed, be used as assist for medical equipment, exercise equipment or communications facilities.

20 Claims, 5 Drawing Sheets

OTHER PUBLICATIONS

Espacenet English Abstract for JP 60-114234 (2 pages).
Espacenet English Abstract for JP 2001-333899 (1 page).
Espacenet English Abstract for JP 60-156631 (1 page).
Espacenet English Abstract for JP 50-94919 (1 page).
Espacenet English Abstract for JP 7-029728 (1 page).
Espacenet English Abstract for JP2005-522292 (1 page).

* cited by examiner

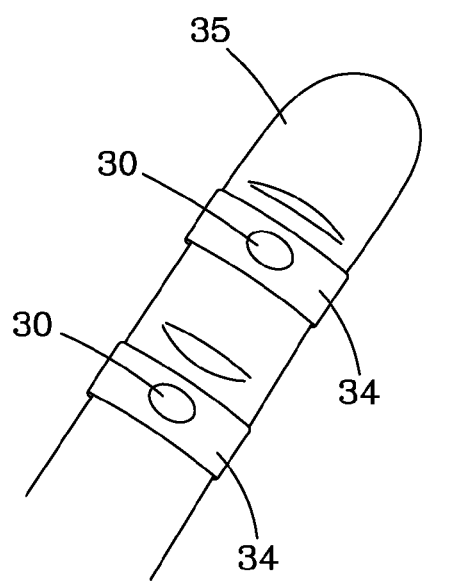
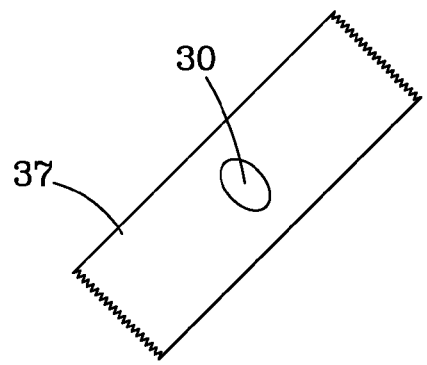
FIG. 6     FIG. 7
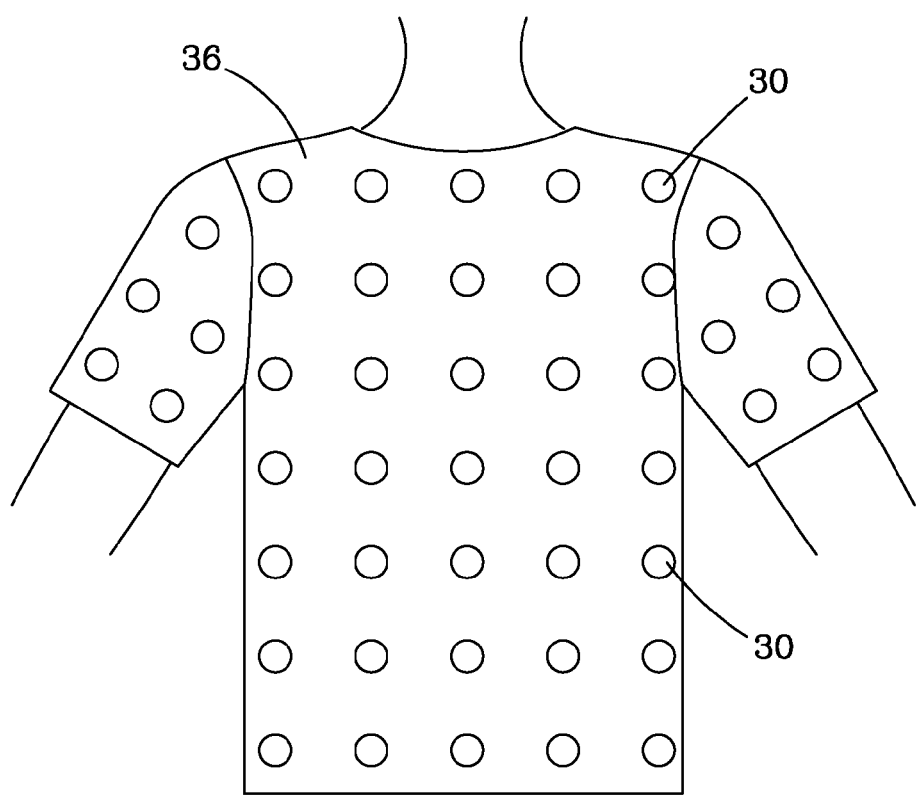
FIG. 8

ELECTRONIC DEVICE AND METHOD OF USING THE SAME

This application is a continuation-in-part of International patent application Ser. No. PCT/CN2005/001520, filed on Sep. 21, 2005, the entire disclosure of which is incorporated herein by reference.

TECHNOLOGICAL ASPECT

This invention involves a human body-testing installation, especially designed to be carried around, and can test any of the following: breath sounds, heart rate, EKG, body fat, sweat wetness, $O_2$ saturation, pulse rate, blood pressure, body temperature, urine sugar, or change in pressure at a point where pressure is applied.

TECHNOLOGICAL BACKGROUND

Well-known electronic devices have been widely used for human body testing purposes, for example, electronic thermometers, electronic blood pressure monitors, lung sound-sensing and heart rhythm-sensing devices. Yet, the aforementioned devices have 3 common disadvantages, namely:
  1. The aforementioned devices are all external devices that are inconvenient to be carried around.
  2. The aforementioned devices are all operated by an on-off switch, to be switched on before use and turned off immediately after. When repetitive and short-time monitoring is needed, as in mountain-climbing, wherein what is actually needed is to take the heart rate every 5 minutes for a duration of 10 seconds, turning the switch on and off repetitively is cumbersome.
  3. In the process of using the aforementioned devices, the user needs to turn on the switch, and then apply pressure on the devices so that it presses on the part to be monitored or tested. For a patient or a busy operator, this is very inconvenient.

Content of Invention:

Facing the above-mentioned problems, this invention aims to provide an electronic device that can be fixed to a user's worn articles, for example clothes, pants, hats, gloves, ties, socks, scarves, etc., so it can be carried around conveniently.

This invention also aims to provide an electronic device with an on-off switch that is designed to be easy to use in repetitive, short-time monitoring or testing.

This invention also aims to provide an electronic device that integrates the actions of switching on and applying pressure on the part to be tested or monitored, into one single action, thereby providing ease of use.

To achieve the above-mentioned aims, one aspect of this invention provides an electronic device and method that include: a resilient piece, a base plate and an electronic source. The resilient piece has an upper conductor; the base plate is connected to the resilient piece, with a space between the resilient piece and the base plate. The base plate is designed with a lower conductor, which is separated from the upper conductor with a crevice. An electronic source connects each of the upper conductor and the lower conductor electrically.

One aspect of the present invention is directed to an electronic device, comprising a resilient piece made of nonconductive and resilient material that is sufficiently elastic to cause an upper conductor, which is electrically conductive, to return to an original position after depression; a base plate made of nonconductive material, a space being provided between the resilient piece and the base plate, the base plate having a lower conductor that is electrically conductive and a side at which the lower conductor can abut the upper conductor; the resilient piece responsive to an applied force by deforming so that the upper conductor and the lower conductors electrically contact each other to switch a circuit on, and removal of the applied force allowing the resilient piece to return to the original position thereby causing the resilient piece and the base plate to separate to switch the circuit off; an intermediate layer that allows the upper and lower conductors to electrically contact, and has a non-conductive portion at one or more ends of the intermediate layer; and one or more tape, ring, clothing or apparel attachment sites around a periphery of the electronic device for directly setting the electronic device within a piece of tape, a ring, or a piece of clothing or apparel.

In one embodiment adhesive tape is located on the base plate and is used to stick the electronic device onto a body joint or around a user's eyes.

In yet another embodiment, the resilient piece has varying thicknesses or different moduli of elasticity according to a desired sensitivity of the electronic device.

In yet another embodiment, the resilient piece is non resilient material and the base plate is resilient material.

In yet another embodiment, the resilient piece and the base plate use the same resilient material.

In yet another embodiment, a sensor device is connected with an electronic source and is used to test breath sounds, heart rhythm, EKG, body fat, sweat wetness, $O_2$ saturation, pulse rate, blood pressure, body temperature, pressure or urine sugar.

In yet another embodiment, a resilient piece is joined between the sensor device and the base plate.

In yet another embodiment, a sensor device electrically connects to a wireless transmission interface for transmitting wirelessly to the outside world test results of a sensor device, and for receiving information from the outside world.

In yet another embodiment, a sensor device electrically connects to a monitor or a speech sound installation.

In yet another embodiment, a sensor device electrically connects to a processor having a threshold time setting, in which force upon the device for more than a set time is stored, displayed or transmitted.

In yet another embodiment, a sensor device electrically connects to a processor that is equipped with functions to turn the sensor device on and off, and change the sensor device's sensing time, sensing frequency, and sensing mode.

In yet another embodiment, the intermediate layer comprises at least one flexible blade, which is located between the resilient place and the base plate, has a fixed end located between the resilient piece and the base plate, and a free end located between the upper conducting plate and the lower conducting plate; the flexible blade being made of nonconductive material.

In yet another embodiment, the intermediate layer Comprises a separated lamina is electrically conductive and connected to an electronic source, said separated lamina being fixed between the base plate and the resilient piece; and a space is provided between it and each of the upper conductor and the lower conductor.

In yet another embodiment, a microphone connected with an electronic source.

In yet another embodiment, a ring is mounted on the base plate, and is configured to be worn on a joint and set on a vehicle's steering wheel.

In yet another embodiment, the base plate is fixed into clothing.

In yet another embodiment, clothing is fixed between the resilient piece and the base plate.

In yet another embodiment, the electronic device is placed between fibers of the clothing.

In yet another embodiment, an area on the clothing where the resilient place is located contains at least one type or functional diagram.

In yet another embodiment, a functional diagram can be made by dyeing or stitching.

In yet another embodiment, the electronic device is one of several electronic devices arranged in an array.

In yet another embodiment, a location of upper conductor and the lower conductor electrical contact is air-permeable from outside of the electronic device.

Another aspect of the present invention is directed to an electronic device comprising a resilient piece, made of non-conductive and resilient material that is sufficiently elastic to cause an upper conductor, which is electrically conductive, to return to an original position after depression; a base plate made of nonconductive material, a space being provided between the resilient piece and the base plate, the base plate having a lower conductor that is electrically conductive and a side at which the lower conductor can abut the upper conductor, the resilient piece responsive to an applied force by deforming so that the upper conductor and the lower conductor electrically contact each Other to switch a circuit on; and removal of the applied force allowing the resilient piece to return to the original position, thereby causing the resilient piece and the base plate to separate to switch the circuit off; a sensor device positioned on an opposite side of the base plate from the side of the base plate at which the lower conductor and upper conductor abut; and one or more tape, ring, clothing or apparel attachment sites around a periphery of the electronic device for directly setting the electronic device within a piece of tape, a ring, or a piece of clothing or apparel.

In yet another embodiment, a direction of the applied force defines an axis along which the sensor device and the base plate are concentrically aligned.

In yet another aspect, the sensor device is connected with an electronic source and is used to test breath sounds, heart rhythm, EKG, body fat, sweat wetness, $O_2$ saturation, pulse rate, blood pressure, body temperature, pressure or urine sugar; a resilient piece is joined between the sensor device and the base plate; the sensor device electrically connects to a wireless transmission interface for transmitting wirelessly to the outside world test results of the sensor device, and receiving information from the outside world; the sensor device electrically connects to a processor having a threshold time setting. In which force upon the device for more than a set time is stored, displayed or transmitted; and either:

(1) at least one flexible blade, which is located between the resilient piece and the base plate, has a fixed end located between the resilient piece and the base plate, and a free end located between the upper conducting plate and the lower conducting plate; the flexible blade being made of nonconductive material; or (2) a separated lamina that is electrically conductive and connected to an electronic source, said separated lamina being fixed between the base plate and the resilient piece; and a space is provided between it and each of the upper conductor and the lower conductor.

In yet another aspect, the present invention is directed to an electronic device comprising: a plate-shaped upper conducting plate, which is electrically conductive; a plate-shaped lower conducting plate, which is electrically conductive; and a nonconductive material, located between the upper conducting plate and the lower conducting plate so that a space is provided between the upper conducting plate and the lower conducting plate, and the upper and lower conducting plates operatively contact each other at one or more points; wherein the non-conductive material forms an intermediate layer that allows the upper conductor and the lower conductor to electrically contact each other.

Yet another embodiment includes a sensor device mounted on an opposite side of the lower contacting plate from the one or more points of the lower conductor and upper conductor contact.

Yet another aspect of the present invention is a method that includes any of the various possible combinations of embodiments shown herein below and above.

EXPLANATION OF ILLUSTRATIONS

After going through the following detailed description by integrated illustrations of a first example embodiment, you will understand more accurately the make-up and special features of this electronic device, which includes:

FIG. 6 shows a schematic diagram of the electronic device's third example embodiment in actual use on the finger;

FIG. 7 shows a schematic diagram of the electronic device's third example embodiment in actual use on the adhesive tape;

FIG. 8 shows a schematic diagram of the electronic device's third example embodiment in actual use on the clothing;

Figure 1:
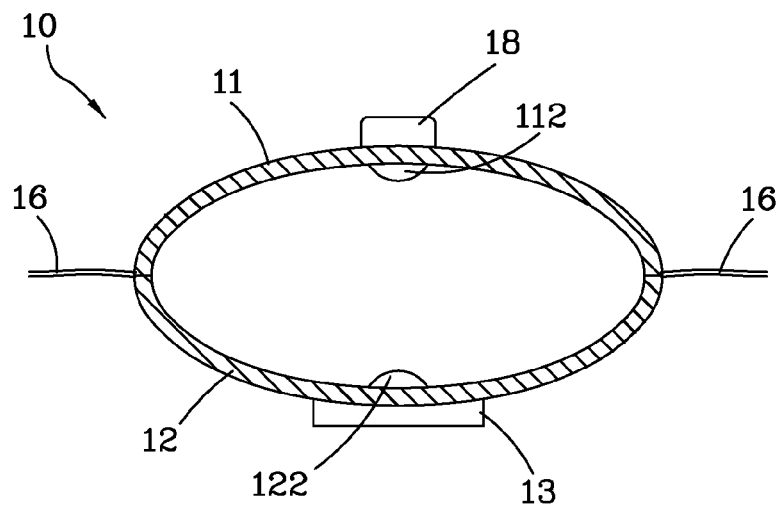
FIG. 1 shows a cut-away view of a first example embodiment of an electronic device of the present invention.

Explanation of the main parts with labels in the illustrations:

| Electronic device 10 | 11 resilient piece | 112 Upper conductor |
|---|---|---|
| | 12 Base plate | 122 Lower conductor |
| | 13 Sensor device | 14 Monitor |
| | 15 Transmission interface | 16 Tested subject's coat |
| | 17 Illustration of functions | 18 Microphone |
| | 19 Processor | |
| Electronic device 20 | 21 Resilient piece | 212 Upper conductor |
| | 213 Hole | 22 Base plate |
| | 222 Lower conductor | 223 Hole |
| | 23 Sensor device | 24 Spring |
| | 25 Tested subject's shirt | 26 Tested subject's skin |
| Electronic device 30 | 31 Upper conducting plate | 32 Lower conducting plate |
| | 33 Nonconductive material | 34 Cover ring |
| | 35 Finger | 36 Clothes |
| | 37 Adhesive tape | |

-continued

| Electronic device 40 | 41 Resilient piece | 412 Upper conductor |
| --- | --- | --- |
| | 413 Hole | 42 Base plate |
| | 422 Lower conductor | 423 Hole |
| | 43 Blade | 44 Sensor device |
| Electronic device 50 | 51 Resilient piece | 512 Upper conductor |
| | 513 Hole | 52 Base plate |
| | 522 Lower conductor | 523 Hole |
| | 53 Nonconductive material | 54 Blade |
| | 55 Sensor device | |
| Electronic device 60 | 61 Resilient piece | 612 Upper conductor |
| | 62 Base plate | 622 Lower conductor |
| | 63 Separated lamina | 64 Sensor device |
| Electronic device 70 | 71 Upper conducting plate | 72 Lower conducting plate |
| | 73 Nonconductive material | 74 Separated lamina |
| | 75 Sensor device | |

Specific Implementing Pattern:

One aspect of the present invention is directed to an electronic device. In the following reference FIGS. 1 through 3, this invention's first example embodiment of the electronic device 10 includes resilient piece 11, base plate 12, sensor device 13, processor 19, monitor 14, transmission interface 15 and an electronic source (not shown). Among which, the resilient piece 11 is like a dome shape, it is facing down, and is made of resilient, nonconductive material. Applying pressure downwards will cause the resilient piece 11 to deform. Romoval of the applied force allows the resilient piece II to return to Its prior shape. The upper conductor 112 is located on the central portion of the lower surface of the resilient piece 11. The base plate 12 is like a dome shapo, and is made of nonconductive material. The dome shape base plate utilizes a disc-to-disc linkage located below the resilient piece 11. There is a space between the resilient piece 11 and the base plate 12. The lower conductor 122 is located on the central portion of the upper surface of the base plate. There is a gap between the lower conductor 122 and the upper conductor 112. The sensor device 13 is located at the lower surface of the base plate 12, and is electrically connected to the lower conductor 122.

Based on this example embodiment, the sensor device 13 is a heart rhythm sensor device which can be used to monitor heart rhythm and subsequently transmit the results to the processor 19. For example, the threshold value in the processor is set for 3 seconds. If the resilient piece 11 is pressed for only 2 seconds, then the processor will ignore and delete the results of this test since it is below the threshold value set in the processor. In other words, if the sensor device is pressed for more than 3 seconds, then the results of this test will be shown on the monitor 14; or the results can be send wirelessly via the transmission interface 15 to the outside world. From here, we can ignore the irrelevant data from tests that are done in too short a time, thereby preventing sensing by mistake. The electronic source provides the needed power to the sensor device 13, the monitor 14 and the transmission interface 15, and is electrically connected to the upper conductor 112 and the lower conductor 122.

Figure 2:
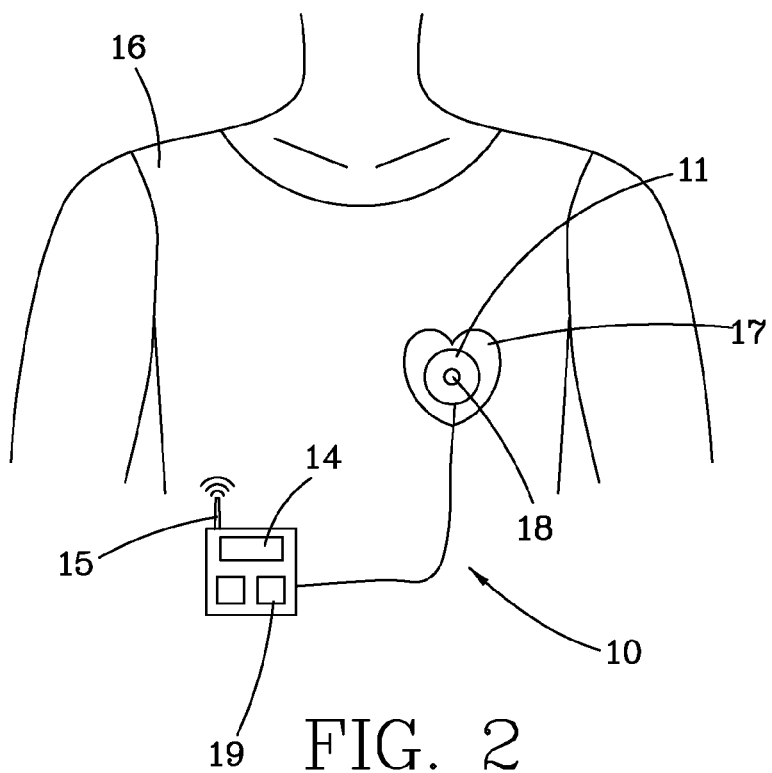
FIG. 2 shows a schematic diagram of this first example embodiment in actual use.
Figure 3:
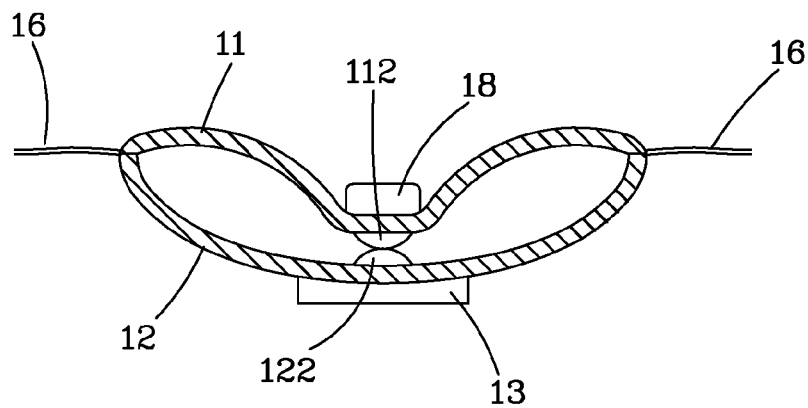
FIG. 3 shows a schematic diagram of the electronic device in FIG. 1 in actual use.

As shown in FIG. 2, the electronic device 10 is directly fixed to the subject's coat 16. As shown in FIG. 1, the coat 16 is fixed between the base plate 12 and resilient piece 11, causing the sensor device 13 to come into direct contact with the part to be sensed, such as the subject's left chest which is closest to the heart. As shown in FIG. 3, during sensing, the subject only needs to apply light pressure on the resilient piece 11, causing it to be deformed, which then causes the upper conductor 112 and the lower conductor 122 to come in direct contact with each other, completing the electrical circuit. When the sensor device 13 is activated, it starts to sense and monitor the subject's heart rhythm, and through the processor 19, decide whether sensing time reaches the threshold of 3 seconds or not. If it does, then the results are shown on the monitor 14, or be transmitted wirelessly to the outside world through the transmission interface 15. On the coat 16 is a functional diagram 17 which indicates the functions of the electronic device 10, and the functional diagram 17 can be dyed or stitched on the resilient piece 11. For example, in this applied example where the sensor device 13 is a heart rhythm sensor, the functional diagram 17 can be in the shape of a heart.

Since this electronic device 10 is directly set to the subject's coat 16, it does away with the inconvenience of carrying a sensor device. And during sensing, the subject needs only to press on the resilient piece with one hand, and turns the switch on and simultaneously causes the sensor device 13 to make contact with the site to be sensed. Because of this, even for repetitive and short-interval testing. It seems very convenient. Also, as the circuit is only powered on when resilient piece 11 is pressed, the circuit is otherwise always open. It decreases the energy consumption and is good for a green policy. Aside from this, this electronic device is also provided with an anti-false sensing feature. In addition, this invention's electronic device improves the disadvantages of similar devices in the market, thereby achieving its goal of our invention.

Moreover, there are several variations to this electronic device 10. For example, the locations of the resilient piece 11 and the base plate 12 can be interchanged. And the elastic base prate 12 is placed on top of the elastic piece 11. Or, both the resilient piece 11 and the base plate 12 use the same resilient material. All these changes give the same results. Secondly, a different thickness or different modulus of elasticity of the resilient piece can change the sensitivity of the electronic device 10. Because of this, during design, we can choose different sensitivity material to be used for the resilient piece based on the practical demands for the sensitivity of the electronic device 10. Several exemplary resilient piece materials include chloroprene rubber (CR) (such as in wetsuits and related water accessories); styrene butadiene rubber (SBR) (for cell phone cases, coolers and the like); a 30%:70% ratio of CR to SBR for sports suits, medical supports, and the like; silicone rubber; nylon; polyester; polypropylene; polyurethane; spandex; Lycra®; and sponge. However, any material suitable for providing a resilient and sufficiently elastic construction can be used.

Furthermore, we can use other types of sensor devices instead of the above-mentioned sensor device 13, for example, those used in sensing lung sound, pulse rate, blood pressure, body temperature, urine sugar, body fat, sweating, ECG, $O_2$ saturation, or pressure sensors. We can also vary the detect portion of the body, change the functional diagram 17 and reset the threshold value in the processor 19 based on the monitor factors. For example, we can use a body temperature sensor device 13 and place it under the armpit, set a longer threshold value of time (for example, 1 minute), for it to have enough time to achieve heat equilibrium. As regards the sensor device for urine sugar, we can place the sensor device near a perineum of a diaper, or dye or stitch a functional diagram thereon, or freely adjust any aspect based on real demands.

In addition, the processor 19 can be equipped with a function to turn the sensor device on and off, change the sensor device's 13 sensing time, sensing frequency, and sensing mode, and/or other parameters based on the user's needs. Or these settings can be set to be activated based on the duration of time the user presses on the resilient piece 11, if it crosses the threshold value set in the processor 19, thereby preventing activation by accidental-touching. Moreover, the transmission interface 15 can be used to receive remote signals for the Purpose of remote activation and inactivation of the sensor device, or to change the procedure of the lest parameters. Regarding the monitor 14, it can be a cellular phone, PDA or a computer that shows the test results. Also, a light-emitting body can be used to emit a warning sign to the people around (such as in the form of a "red cross" or the number "119") whenever the sensor device 13 senses an abnormal result, such as an overly high blood pressure or sudden stop of the heartbeat. Or, signals can be sent via the transmission interface 15 to relatives far away, or directly call an ambulance. And also, the electronic device 10 can be equipped with a microphone 18 in the resilient piece 11 and connected electrically with the upper conductor 112, to allow the user to directly communicate with or seek help from the outside world via the transmission interface 15. The place where resilient piece 11 is located on the coat 16 can be printed with a functional diagram 17 to differentiate between emergency articles and communication articles. Included in the functional diagram 17 are illustrations of a red cross, ambulance and relatives.

Aside from these, when the electronic device 10 is designed to be an EKG or blood pressure sensor, the time needed for testing needs to be at least 1-2 minutes. Because of this, the subject's coat 16 can be equipped with a self-inflatable airbag. When the subject presses on the resilient piece 11, the upper conductor 112 comes into contact with the lower conductor 122, causing the inflatable bag to self-inflate thereby pressing the sensor device 13 against the skin of the part to be tested. Or the subject's shirt can be designed to be tight-fitting, which can lessen inconvenience on the subject who needs to maintain a proper position. This increases the ease of use.

Figure 4:
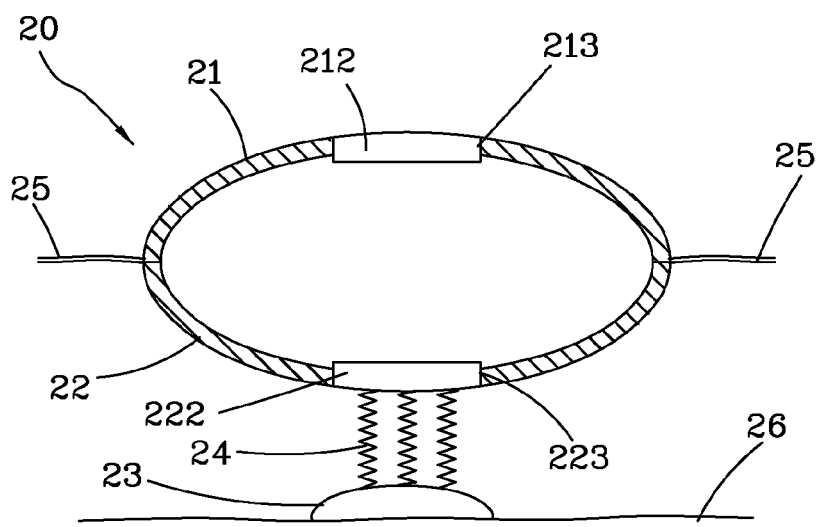
FIG. 4 shows a cut-away view of a second example embodiment of an electronic device of the present invention.
Figure 5:
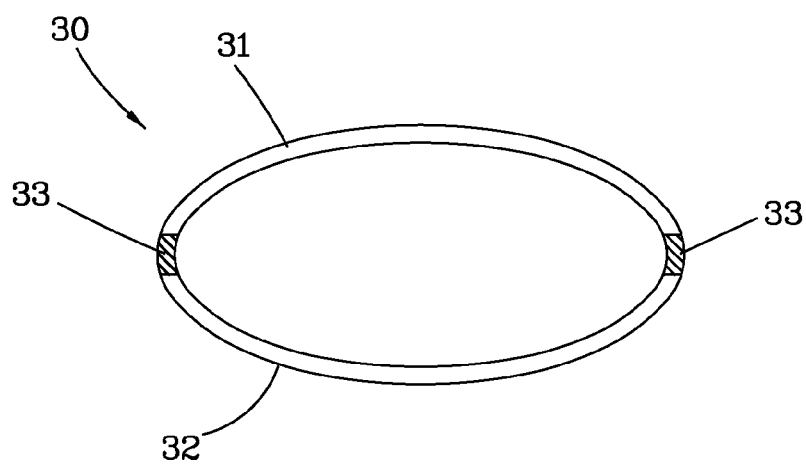
FIG. 5 shows a cut-away view of a third example embodiment of an electronic device of the present invention.

As shown in FIG. 4, this invention's second example embodiment of the electronic device 20 includes a resilient piece 21, base plate 22, sensor device 23, 3-row spring 24, monitor (not shown), and electronic source (not shown). Among which, the resilient piece 21 is like a dome shape and made of resilient, nonconductive material. In the disk center of the resilient piece 21, the upper conductor 212 and a hole 213 are located, where the upper conductor 212 is mounted. The base plate 22 is also like a dome shape, is made of resilient, nonconductive material, and is connected to the resilient piece between which there is a space. In the disk center of the base plate 22, the lower conductor 222 and an hole 223 are located, where the lower conductor 222 is mounted. There is a crevice between the lower conductor 222 and the upper conductor 212. The applied example of the sensor device 23 is a lung sound sensor, which is electrically connected to the lower conductor 222. This sensor device 23 is used to test human lung sound, and shows the test results on the monitor. The 3-combined spring 24 and the sensor device 23 and the base plate 22 are joined together. The electronic source provides the needed power to the sensor device 23 and the monitor, and is electrically connected to the upper conductor 212 and the lower conductor 222.

Fixing the electronic device 20 directly on the subject's shirt 25, makes it so that the sensor device 23 is pressing down directly on the part to be tested 26. During testing, pressing lightly on the resilient piece 21 promotes contact between the upper conductor 212 and the lower conductor 222, thereby turning the electrical circuit on. As the sensor device 23 is activated, it starts to test the subject's lung sound. Utilizing this type of structure, even if the subject performs extreme exercise, thereby deviating the position of the resilient piece 21 and the base plate 22 from the area to be tested, the sensor device 23 can still remain fixed to the site to be tested. For this reason, not only can the electronic device 20 maintain its active test status at all times, but also cannot be affected by the subject doing exercise and thereby moving the sensor device 23 from the tested site 26, causing error. The electronic device 20 can also be carried around conveniently, and be operated by one hand even during repetitive, short-interval testing. This is extremely convenient.

Referring to FIGS. 5 through 8, this invention's third example embodiment of the electronic device 30 includes an upper conducting plate 31, lower conducting plate 32, nonconductive material 33, processor (not shown), monitor (not shown), and electronic source (not shown). Among which, the upper conducting plate 31 and the lower conducting plate 32 is like a dome shape and are made of resilient conductive material. The nonconductive material 33 is ring-shaped. The edges of the disks of the upper conducting plate 31 and the lower conducting plate 32 are fixed separately to the upper and lower edges of the nonconductive material 33. The upper conducting plate 31 and lower conducting plate 32 are separated from the nonconductive material to form a space. The processor is electrically connected to the upper Conducting plate 31 and the lower conducting plate 32 separately. It can distinguish whether the circuit is on or off between the upper conducting plate 31 and the lower Conducting plate 32, and can process this mutual electrical conductance signal and Show it on the monitor. The electronic source provides the power needed for the processor and the monitor, and is electrically connected to the upper conducting plate 31 and the lower conducting plate 32.

The electronic device 30 is installed to the ring 34 to be put on the subject's finger 35 near the joint. This can be used in deaf-mute persons as a means of communicating with each other, and similarly among medical personnel in the operating room. If the subject wishes to express a personal opinion, the only needs to bend his finger, forcing the upper conducting plate 31 and the lower conducting plate 32 to change shape, thereby coming into contact with each other, completing an electrical circuit. Afterwards, when the processor receives this electrical conducted signal, it processes it and shows it on the monitor. For example, it can be designed in such a way that bending the finger once means "Yes", and twice means "No", or three times or more or at different intervals to mean other different words, based on the needs of the user. Moreover, the monitor can be equipped with speakers, which can directly broadcast the user's opinion in spoken language for others to hear. Another thing is, as shown in FIG. 7, we can use the adhesive tape 37 to fix the electronic device 30 on the eyelids, hence allowing a special group of patients (quadriplegics) to express their thoughts through blinking. Electronic device 30 is thus used in conjunction with a speech sound installation.

Besides, this invention's third example embodiment of the electronic device 30 can have other uses. For example, we can have several electronic devices 30 placed near the wrist joints, elbow joints, or the knee joints, and share a common processor to process different signals as a whole. Utilizing this arrangement, the electronic device 30 can be used as an exercise-assist equipment, helping beginners learn essential actions, just like learning to play golf, where the different electronic devices 30 on the different joints will help us determine if the user's posture is correct, and show it on the monitor. It can even show clearly the position of an incorrect posture, hence improving the user's learning results.

Again as shown in FIG. 8, we can use several electronic devices 30 and arrange them in matrix array form, and place them between the fibers of the clothes 36, which critically ill, vegetative and chronically bed-ridden patients can wear. With the help of the test results, we can promptly know the condition of body areas that are subjected to pressure under prolonged time in these patients, and can alert nurses in advance to help the patients, thereby preventing bedsores or eczema. Moreover, we can install the electronic device 30 to a ring placed on a steering wheel as a tool to assist drivers. In this case, the electronic device will be used to test if the driver is grasping the steering wheel correctly. If not, the monitor will immediately show a warning signal to alert the driver, thereby preventing accidents.

Figure 9:
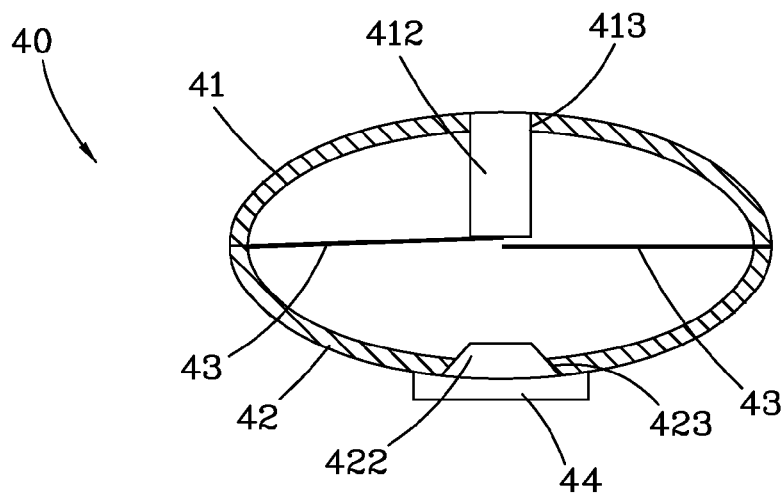
FIG. 9 shows a Cut-away view of a fourth example embodiment of an electronic device of the present invention.
Figure 10:
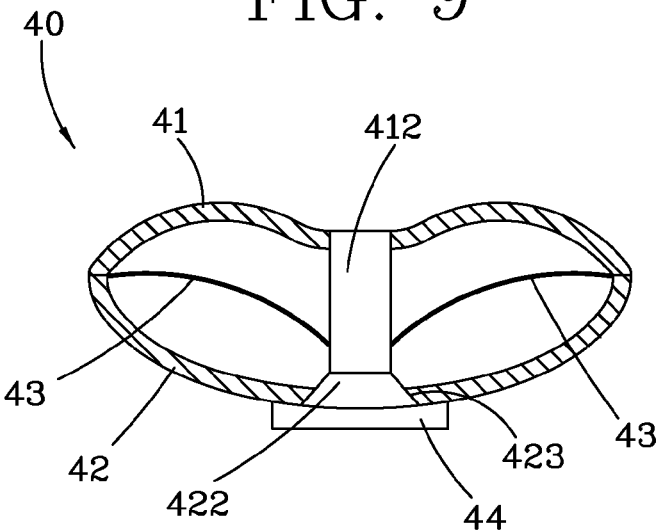
FIG. 10 shows a schematic diagram of the electronic device in FIG. 9 in actual use.

As shown in FIGS. 9 through 10, this invention's fourth example embodiment of the electronic device 40 includes a resilient piece 41, base plate 42, two blades 43, sensor device 44, monitor (not shown), and electronic source (not shown). Among which, the resilient piece of forms a dome shape and is made of resilient, nonconductive material. In the disk center of the resilient piece 41, the upper conductor 412 and an hole 413 are located, where the upper conductor 412 is mounted. The base plate 42 is also dome-shaped, is made of resilient, nonconductive material, and is connected to the resilient piece 41, between which there is a space. In the disk center of the base plate 42, the lower conductor 422 and a hole 423 are located, where the lower conductor 422 is mounted. The two blades 43 are each rectangular, board-like plates, and are made of flexible, nonconductive material. Its fixed end is fixed on the spot where the elastic piece 41 and the base plate 42 are joined, while its free end is located between the upper conductor 412 and the lower conductor 422. The distance between the two blades 43 and the upper conductor 412 is smaller than the distance between the two blades 43 and the lower conductor 422. The sensor device 44 is located on the lower surface of the base plate 42, and is electrically connected to the lower conductor 422. The sensor device is used to test the subject's physiological status, and the results are shown on the monitor. The electronic source provides the needed power to the sensor device 44 and the monitor, and is electrically connected to the upper conductor 412 and the lower conductor 422.

When the electronic device 40 is fixed to the subject's garment, he only needs to press lightly on the resilient piece 41, causing it to deform and change shape, leading to the upper conductor 412 to push apart the two blades 43 and coming into contact with the lower conductor 422, completing the electrical circuit on, as shown in FIG. 10. When the sensor device 44 is activated, it starts to test. If the subject is in the process of moving, and unintentionally pulls tightly his shirt where the electronic device 40 is located, this will impel the base plate 42 to change shape. The lower conductor 422 will not be able to come into contact with the upper conductor 412 because it is separated by the two blades 43. Hence, this will prevent testing by mistake and power wastage. Based on this, the electronic device 40 not only allows the subject to be tested at any time based on his needs, but also can prevent testing by mistake due to the subject's exaggerated movements.

Figure 11:
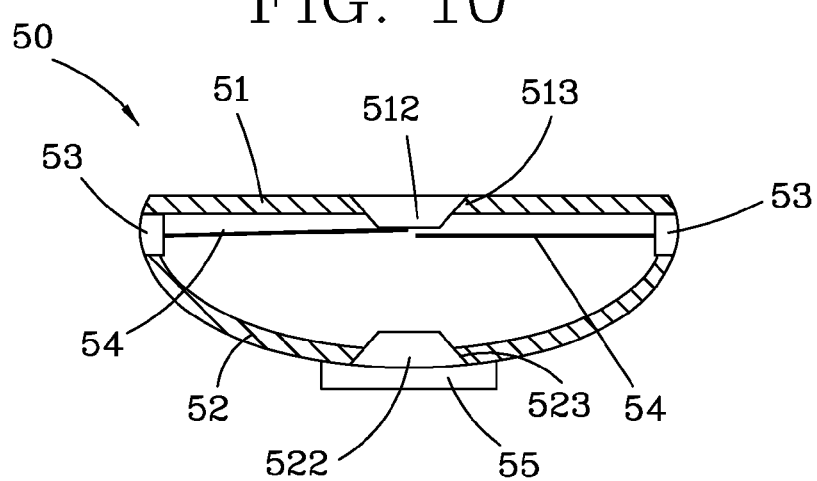
FIG. 11 shows a cut-away view of a fifth example embodiment of an electronic device of the present invention.

As shown in FIG. 11, this invention's fifth example embodiment is electronic device 50, which includes a resilient piece 51, base plate 52, nonconductive material 53, two blades 54, sensor device 55, monitor (not shown), end electronic source(not shown). Among which, the resilient piece 51 is round, lamina-shaped and made of resilient nonconductive material. In the center of the resilient piece 51 are the upper conductor 512 and an opening 513 where the upper conductor 512 is mounted. The base plate 52 is like a dome shape and is made of resilient nonconductive material. In the disk center are located the lower conductor 522 and an hole 523 where the lower conductor 522 is mounted. The nonconductive material 53 is ring-shaped. The resilient piece 51 and the base plate 52 are fixed on the upper and lower edges of the nonconductive material 53 respectively. There is a space between the upper conductor 512, the lower conductor 522 and the nonconductive material 53. The two blades 54 are each rectangular, board-like plates, and are flexible, nonconductive material. Its fixed end is fixed on the nonconductive material 53, while its free end is located between the upper conductor 512 and the lower conductor 522. The distance between the two blades 54 and the upper conductor 512 is smaller than the distance between the two blades 54 and the lower conductor 522. The sensor device 55 is located on the lower surface of the base plate 52, and is electrically connected to the lower conductor 522. The sensor device is used to test the subject's physiological status, and the results are shown on the monitor. The electronic source provides the needed power to the sensor device 55 and the monitor, and is electrically connected to the upper conductor 512 and the lower conductor 522.

This application example has a similar effect as the fourth application example. The user simply has to press on the resilient piece 51, causing the upper conductor 512 to change the shape of the two blades 54, thereby coming into contact to the lower conductor 522 it is on. On the other hand, if the user mistakenly presses on the base plate 52, the lower conductor 522 will be obstructed by the two blades 54, preventing electrical connection with the upper conductor 512.

Figure 12:
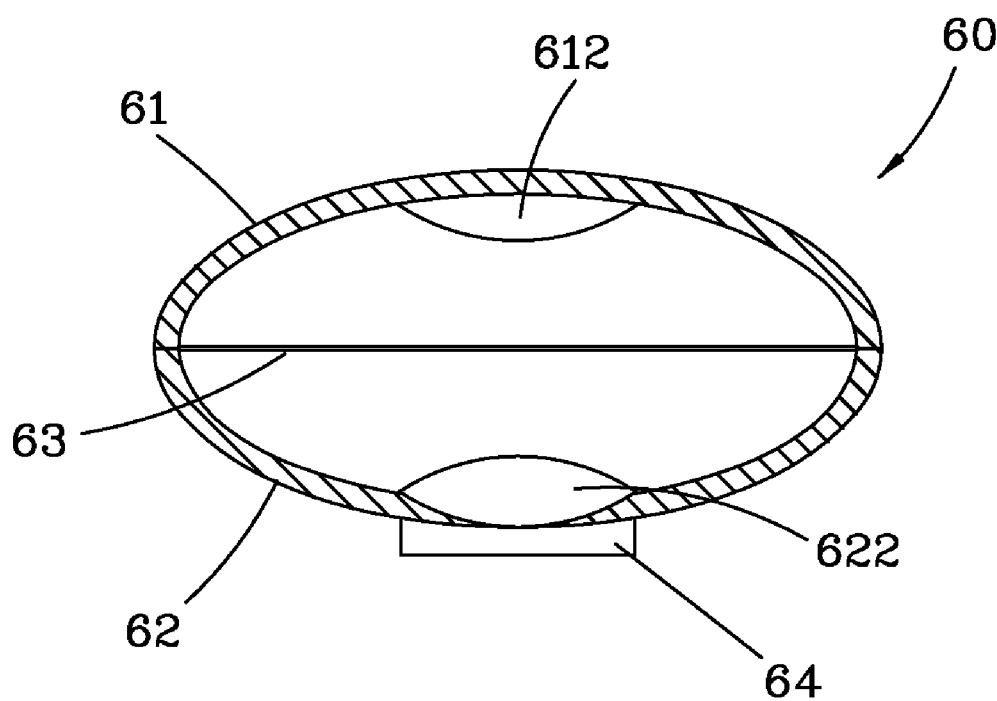
FIG. 12 shows a cut-away view of a sixth example embodiment of an electronic device of the present invention.

Referring to FIG. 12, this invention's sixth example embodiment of the electronic device 60 includes an resilient piece 61, base plate 62, separated lamina 63, sensor device 64, monitor (not shown), processor (not shown) and electronic source (not shown). Among which, the resilient piece 61 is like a dome shape and is made of resilient, nonconductive material. In the center portion of the underside of the resilient piece 61 is the upper conductor 612. The base plate 62 is like a dome shape and is made of resilient nonconductive material. In the disk center are located the lower conductor 622. The separated lamina 63 is designed to include conductible material, so it can be conductive at a fixed on the spot where the resilient piece 61 and the base plate 62 are joined. There is a crevice between the separator board 63 and both the upper conductor 612 and the lower conductor 622. The sensor device 64 is fixed on the lower surface of the base plate 62, and is electrically connected with the lower conductor 622. It is used to test the subject's physiological status and shows the results on the monitor. The processor is electrically connected to each of the following: upper conductor 612, the lower conductor 622, separated lamina 63 and sensor device 64, and is pre-installed with a deciding program. The contents of the program are as follows:

1. When the separated lamina 63 contacts first with the upper conductor 612, followed by the lower conductor 622, the sensor device 64 is activated, and starts to test;
2. when the separated lamina 63 contacts first with the lower conductor 622, followed by the upper conductor 612, no action is taken;
3. Under other circumstances, no action is taken without exception.

The electronic source provides the needed power to the sensor device 64, monitor and processor.

The electronic device 60 can be installed in the user's clothes. When the user lightly presses the resilient piece 61, it and the base plate 62 will change shape, causing the upper conductor 612 to come into contact first with the separated lamina 63, followed by the lower conductor 822. When the processor receives this information, it commands the sensor device 64 to start testing. On the contrary, when there is exaggerated movement from the user. causing the electronic device 60 to rub against the skin, there is an upward push from the Skin, causing the lower conductor 622 to come into contact first with the separated lamina 63, followed by the upper conductor 612 contacted with the separated lamina 63. The processor will ignore this signal, thereby preventing the electronic device 30 to test by mistake.

Figure 13:
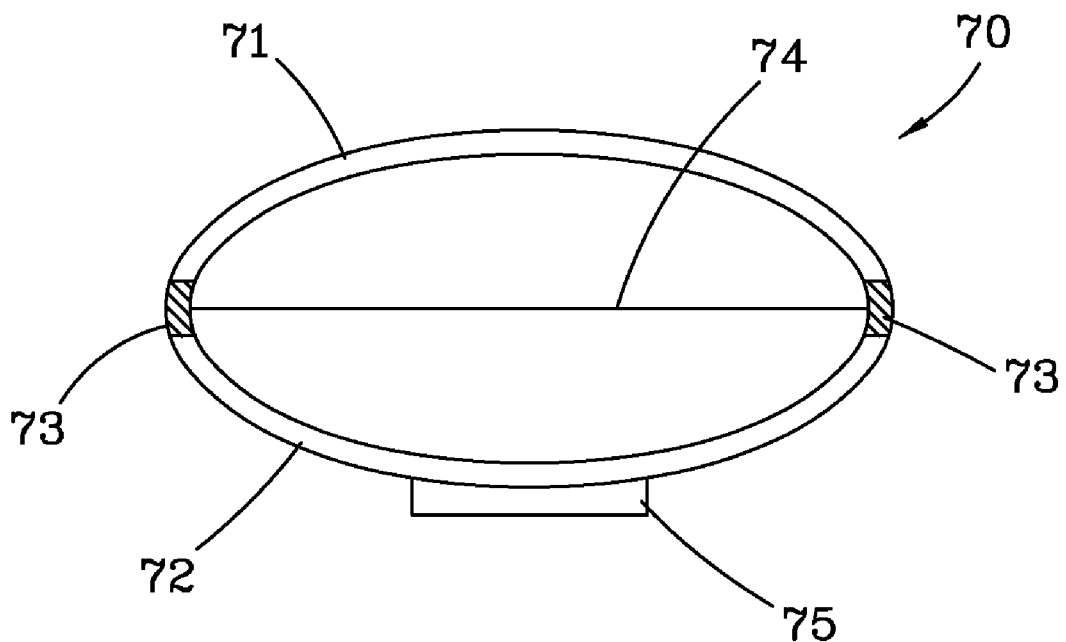
FIG. 13 shows a Cut-away view of a seventh example embodiment of an electronic device of the present invention.

Comparing FIG. 13, this invention's seventh example embodiment of the electronic device 70 includes the upper conducting plate 71, the lower conducting plate 72, nonconductive material 73, separated lamina 74, sensor device 75, processor (not shown), output device (not shown), and a electronic source (not shown). Among which, the upper conducting plate 71 and the lower conducting plate 72 are dome-shaped, and are made of resilient, conductive material. The nonconductive material 73 forms a ring shape, and the upper conducting plate 71 and lower conducting plate 72 are fixed to the upper and lower edges of the nonconductive material 73 respectively. The separated lamina 74 is located inside the nonconductive material 73, and is separated from the upper conducting plate 71 and lower conducting plate 72 by a crevice. The sensor device 75 is fixed on the lower surface of the lower conducting plate 72, and is electrically connected to the lower conducting plate 72. The sensor device is used to test the subject's physiological status. The processor is electrically Connected to each of the following: upper conducting plate 71, the lower conducting plate 72, separated lamina 74 and sensor device 75, and is pre-installed with a deciding program. The contents of the program are as follows:

1. When the separated lamina 74 contacts first with the upper conducting plate 71, followed by the lower conducting plate 72, the sensor device 75 is activated, and starts to test;
2. When the separated lamina 74 contacts first with the lower conducting plate 72, followed by the upper conducting plate 71, no action is taken;
3. Under other circumstances, no action is taken without exception. The electronic source provides the needed power to the sensor device 75, monitor and processor.

Based on the above, this application example has the same effect as the sixth application example. If the user presses on the upper conducting plate 71, causing it to come into contact first with the separated lamina 74, followed by the lower conducting plate 72 corning into contact with the separated lamina 74, the processor will receive this signal and activate the sensor device 75 to start testing. On the contrary, if the signal is first due to the lower conducting plate 72 pressed by mistake, the processor will Ignore this signal. Hence, the electronic device 70 has both the advantageous features of testing at anytime and preventing testing by mistake.

A second aspect of the present invention is directed to a method that provides the electronic device described in the various interchangeable elements and embodiments above.

While it is apparent that the Illustrative embodiments of the invention disclosed herein fulfill the objectives of the present invention, it is appreciated that numerous modifications and other embodiments may be devised by those skilled in the art. Additionally, feature(s) and/or element(s) from any embodiment may be used singly or in combination with other embodiment(s). Therefore, it will bo understood that the appended claims are intended to cover all such modifications and embodiments that would come within the spirit and scope of the present invention.

What is claimed is:

1. An electronic device comprising:
    an upper layer made of a nonconductive material;
    a lower layer made of a nonconductive material;
        wherein at least one of the upper layer and the lower layer is made of a resilient material having a sufficient elasticity such that it will return to an original shape after being deformed,
        wherein the upper layer comprises an upper conductor on the side facing the lower layer and the lower layer comprises a lower conductor on the side facing the upper layer and a space is provided between the upper conductor and the lower conductor such that the upper conductor and the lower conductor are not in contact until a force is applied to deform the at least one of the upper layer and the lower layer; and
    a sensor device for human body testing located on the lower layer and connected with the lower conductor.

2. The electronic device of claim 1 wherein the upper layer and/or the lower layer made of the resilient material has varying thicknesses or different moduli of elasticity according to a desired sensitivity of the electronic device.

3. The electronic device of claim 1 wherein the upper layer and the lower layer are both resilient are made of same or different resilient materials.

4. The electronic device of claim 1 wherein the sensor device is capable of detecting breathing sounds, heart rhythm, EKG, body fat, sweat wetness, $O_2$ saturation, pulse rate, blood pressure, body temperature, pressure, or urine sugar.

5. The electronic device of claim 1, further comprising a resilient piece joined between the sensor device and the lower layer.

6. The electronic device of claim 1, further comprising a wireless transmission interface for transmitting wirelessly test results of the sensor device.

7. The electronic device of claim 1, further comprising a monitor or a light-emitting device.

8. The electronic device of claim 1, further comprising a processor that is equipped with functions to turn the sensor device on and off, or to change sensing time, sensing frequency, and/or sensing mode of the sensor device.

9. The electronic device of claim 1, further comprising at least one flexible blade located between the upper layer and the lower layer, wherein the at least one flexible blade has a fixed end located proximate a joint between the upper layer and the lower layer and a free end located between the upper conductor and the lower conductor; wherein the at least one flexible blade being made of a nonconductive material.

10. The electronic device of claim 1, further comprising a separated lamina that is electrically conductive and fixed between the lower layer and the upper layer; and wherein a space is provided between the separated lamina and each of the upper conductor and the lower conductor.

11. The electronic device of claim 1, further comprising a microphone connected with an electronic source.

12. The electronic device of claim 1, further comprising a ring that is mounted on the upper or lower layer and configured to be worn near a joint or set on a vehicle's steering wheel.

13. The electronic device of claim 1, further comprising a garment or a piece of cloth to which the lower layer is affixed.

14. The electronic device of claim 13, wherein the piece of cloth is fixed between the upper layer and the lower layer.

15. The electronic device of claim 13 wherein the electronic device is placed between fibers of the piece of cloth or the garment.

16. The electronic device of claim 13 wherein the garment comprises an inflatable airbag for pressing the sensor device against a user wearing the garment.

17. The electronic device of claim 1 wherein the electronic device is one of several electronic devices arranged in an array.

18. The electronic device of claim 1, further comprising:
one or more tape, ring, clothing or apparel attachment sites around a periphery of the electronic device for setting the electronic device on a piece of tape, a ring, or a piece of clothing or apparel.

19. The electronic device of claim 18 wherein a direction of the applied force defines an axis along which the sensor device and the lower layer are aligned.

20. An electronic device comprising:
a plate-shaped upper conductor;
a plate-shaped lower conductor;
a nonconductive intermediate layer, located between the upper conductor and the lower conductor such that a space is provided between the upper conductor and the lower conductor; and
a lamina layer disposed between the upper conductor and the lower conductor,
wherein the lamina layer can contact the upper conductor or the lower conductor when a force is applied, and
wherein the electronic device is disposed on a garment or an article to be worn by a user proximate a joint to detect a user posture change.

* * * * *